United States Patent [19]

Meredith, Jr.

[11] Patent Number: 5,768,471
[45] Date of Patent: Jun. 16, 1998

[54] OPTICAL ANALYZER FOR MEASURING REFLECTIVITY OF MOVING SUBSTRATE

[75] Inventor: William A. Meredith, Jr., Faribault, Minn.

[73] Assignee: Viratec Thin Films, Inc., Faribault, Minn.

[21] Appl. No.: 567,927

[22] Filed: Dec. 6, 1995

[51] Int. Cl.$^6$ ........................................... G01N 21/55
[52] U.S. Cl. ................................................. 356/445
[58] Field of Search ........................... 356/445; 385/43, 385/31, 900; 250/227.11

[56] References Cited

U.S. PATENT DOCUMENTS

| | | | |
|---|---|---|---|
| 3,370,502 | 2/1968 | Wilks, Jr. | 88/14 |
| 4,019,066 | 4/1977 | Lucas et al. | 356/345 |
| 4,697,867 | 10/1987 | Blanc et al. | 385/43 |
| 4,729,621 | 3/1988 | Edelman | 385/43 |
| 5,142,596 | 8/1992 | Mizuuchi et al. | 385/43 |
| 5,252,836 | 10/1993 | Matthews et al. | 356/445 |
| 5,254,858 | 10/1993 | Wolfman et al. | 250/339 |
| 5,530,781 | 6/1996 | Takahashi | 385/43 |

*Primary Examiner*—David C. Nelms
*Assistant Examiner*—Amanda Merlino
*Attorney, Agent, or Firm*—Fish & Richardson P.C.

[57] ABSTRACT

An optical analyzer measuring the reflectivity of a moving article in an in-line sputtering deposition system. The optical analyzer includes a light source which provides a light beam. Light is reflected from an optical coating of a moving article into a concentrator, which captures and directs the reflected light to a detector. The analyzer may be mounted in an evacuable chamber in which the end walls have openings to allow passage of the article.

13 Claims, 5 Drawing Sheets

OPTICAL ANALYZER FOR MEASURING REFLECTIVITY OF MOVING SUBSTRATE

BACKGROUND OF THE INVENTION

The present invention relates generally to optical analyzers which measure reflectivity, and more particularly to optical analyzers which measure the reflectivity of thin films on moving substrates.

The thickness of variations of an optical coating, such as multilayer antireflection (AR) coating, generally must be held to within about plus or minus one percent to maintain the coating's desired optical properties. An in-line sputtering deposition system may be used to economically mass produce coated articles.

In a typical in-line sputtering deposition system, substrates to be coated are passed through a series of vacuum chambers in the deposition system. The substrates are often transported beneath sputtering cathodes by sets of rotating rollers. As a substrate passes from one chamber to the next, the sputtering cathodes successively deposit selected materials on the substrate to gradually build up the optical coating.

It is desireable to periodically monitor the optical coating by shining a light beam at the optical coating, measuring the amount of light transmitted or reflected, and comparing the result to the values expected at that stage of the deposition process. This monitoring procedure ensures that the deposition system is operating properly and that the optical coating will have the desired optical properties at the end of the process.

One method of performing the measurements would be to remove the substrates from the in-line sputtering apparatus between the different deposition stages. However, this would negate the economic advantages of "assembly line style" in-line sputtering. Consequently, it is preferable to measure the transmission and reflection of the optical coating while the substrate is in the sputtering apparatus.

A simple in-line prior art system 10 to measure the transmission of an optical coating, is shown in FIG. 1. Light from a source 12 is formed by a lens 14 into a beam 16. Light beam 16 passes through an optical coating 20 and the transparent substrate 24, and is directed by a lens 26 to an optical detector 28.

Theoretically, one could convert transmission measuring system 10 into a reflection measuring system 20 as shown in FIG. 2A. Light from a source 32 would be formed by a lens 34 into a collimated or focused light beam 36 aimed at substrate 44. Light beam 36 would reflect off optical an optical coating 40 to form a reflected beam 38. A lens 46 would focus light beam 38 on an optical detector 48. In reality, such a reflectivity analyzer suffers from a serious defect.

As the substrate moves on the rollers, it may undulate and vibrate, or "wobble". Wobbling of the substrate changes the angle of reflection of the light beam from the optical film. Consequently, the reflected light beam will be deflected away from the detector apparatus. First, the measured reflectivity will be lower than the actual reflectivity because the light beam is not centered on the detector. Second, since the wobbling may change with time, the accuracy of the measurement cannot be improved.

Unfortunately, one cannot use the reflective optical system 30 shown by FIG. 2A for a moving substrate 44. If substrate 44 drops, as shown in FIG. 2B, or if substrate 44 tilts, as shown in FIG. 2C, then the position of reflected light beam 38 changes and it will no longer be directed to detector 48 by lens 46. Changes in the reflection angle of just 0.20° may create a pronounced loss of signal, ruining the reliability of the reflectance measurement.

In view of the foregoing, it is an object of the present invention to provide an optical analyzer which accurately measures the reflectivity of an optical coating on a moving substrate in an in-line sputtering apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to an optical analyzer. The optical analyzer has a light source which provides a light beam. A moving article with a reflective optical coating thereon is located in the path of the light beam. Light is reflected from the optical coating into a concentrator. The concentrator captures and directs the reflected light to a detector.

BRIEF DESCRIPTION OF THE DRAWING

The accompanying drawings, which are incorporated in and constitute a part of the specification, schematically illustrate a preferred embodiment of the invention, and together with the general description given above and the detailed description of the preferred embodiment given below, serve to explain the principles of the invention.

DESCRIPTION OF THE PREFERRED EMBODIMENTS

Figure 3:
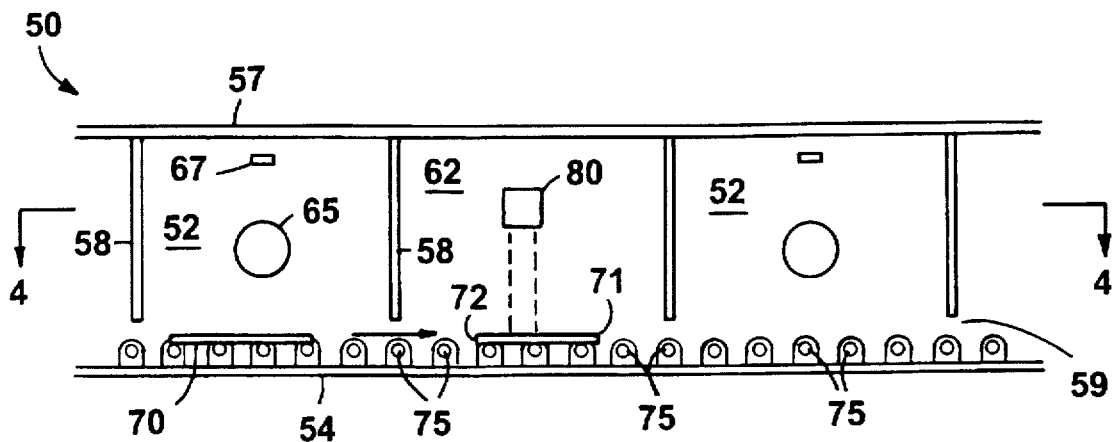
FIG. 3 is a schematic side view of an in-line deposition system containing the optical analyzer of the present invention.
Figure 4:
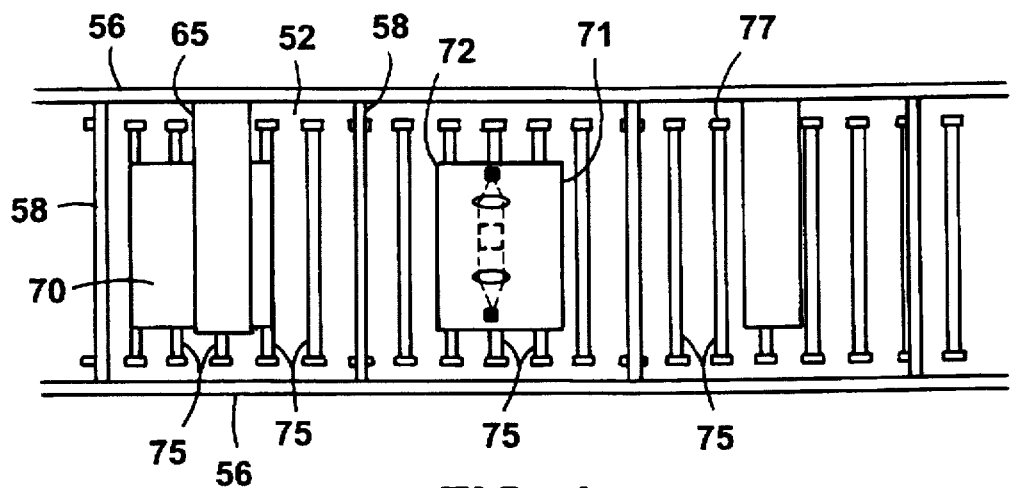
FIG. 4 is a schematic top view taken along line 4—4 of FIG. 3.

An in-line deposition system 50 utilizing the present invention is shown by FIGS. 3 and 4. The deposition system 50 consists of a series of deposition chambers. Each chamber is defined by a base or floor 54, side walls 56, and removable top 57. Adjacent chambers are separated by internal walls or bulkheads 58 with openings 59 to permit the passage of a substrate 70. The chambers are maintained at a near-vacuum by pumps (not shown). Sputtering devices, such as a rotating cathode magnetron 65 and anode 67, are mounted in chambers 52. The construction and mounting of magnetrons is described in U.S. Pat. Nos. 5,200,049, and 5,100,527, both assigned to the assignee of the present invention, the entire disclosures of which are incorporated by reference.

The optical analyzer 80 is preferably located in an "interstage" chamber 62 in which sputtering devices have not been installed. In an alternate embodiment in which the optical analyzer is located in a deposition chamber 52, there is a danger of thin film sputtered material accumulating on the optical parts.

Substrate 70 is supported by rollers 75, typically about a foot apart, which are mounted on spindles 77. Rollers 75 rotate to carry substrate 70 through each chamber 50 and beneath the cathodes 65. Rollers 75 may include bumps, protrusions, or other features to increase friction between substrate 70 and rollers 75. However, there are a number of factors which cause the top surface of substrate 70 to move erratically. First, there is not a perfect grip between substrate 70 and rollers 75, so the substrate 70 may wobble. Second, the leading edge 71 and trailing edge 72 of substrate 70 are unsupported and will tend to droop. As substrate 70 moves in the direction of arrow A, the drooping leading edge 72 will strike the next roller 75, and a shock will be sent through substrate 70. Third, the movement of substrate 70 over rollers 75 tends to create a "porpoising effect" which causes the substrate to vibrate. Fourth, heat differences may cause the various components of in-line system 50 to expand or contract, changing the height of substrate. In total, substrate 70 may easily vary in tilt by one degree and in height by a quarter of an inch.

Figure 5:
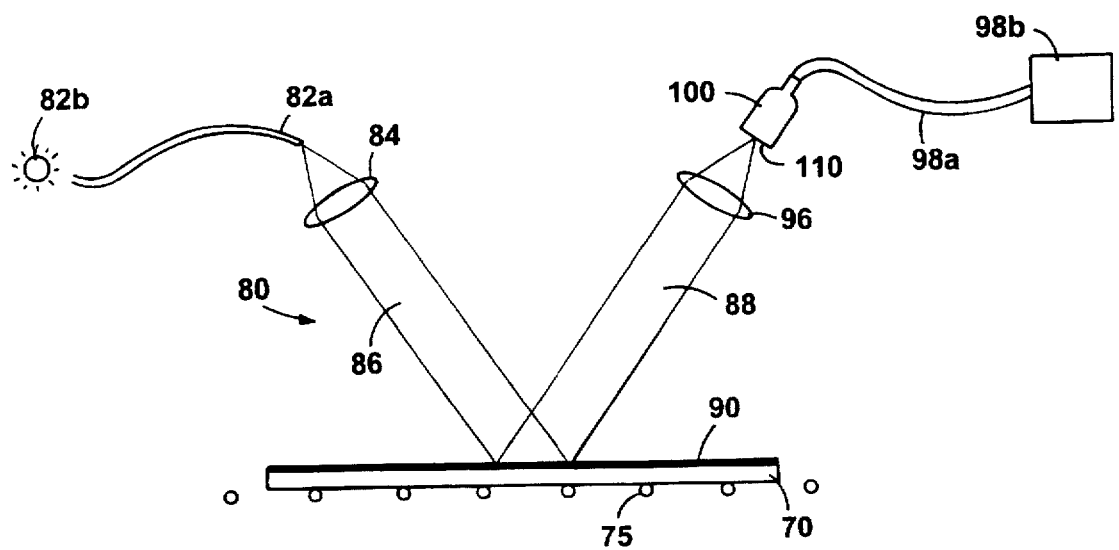
FIG. 5 is a schematic illustration of the reflection analyzer of the present invention.
Figure 6:
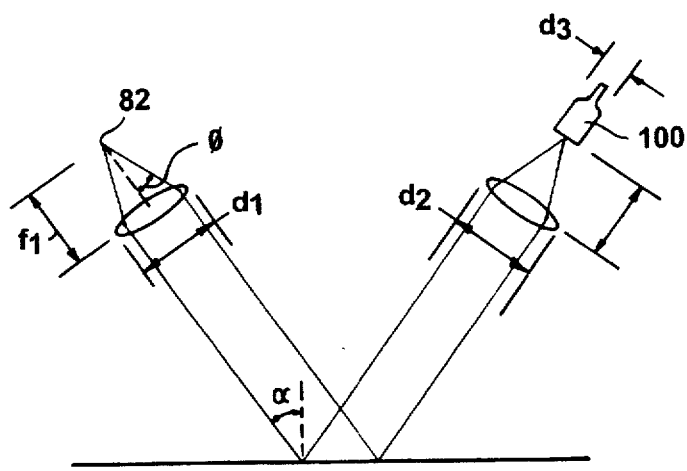
FIG. 6 is a schematic diagram of the optics of the reflection analyzer of the present invention.

Optics of optical analyzer 80 are shown by FIGS. 5 and 6. Light is emitted from a source 82 with a spread $\phi$ of about twenty-two degrees. Preferably, source 82 includes an optical fiber 82a, three millimeters in diameter, carrying light from some wide band spectrum illuminator 82b, such as a xenon arc lamp. Light from source 82 is focused by a lens 84 (which can include multiple pieces) into light beam 86. Lens 84 preferably has a diameter $d_1$, of about one inch, and a focal length $f_1$, of about two inches. Lens 84 may either collimate or focus the light. Light beam 86 is directed to substrate 70 which is moving on rollers 75. The angle of incidence $\alpha$ of light beam 86 on substrate 70 is about ten degrees, but may change depending on the motion of substrate 70. Light beam 88 is reflected from optical coating 90 on substrate 70, passes through a lens 96, and is focused into a concentrator 100. Lens 96 is equal in size, or somewhat larger than lens 84, and preferably has a diameter $d_2$ of about 1.25 to 1.5 inches and a focal length $f_2$ equal to about twice diameter $d_2$. The lenses 84 and 96 are located as close as possible, without the parts colliding.

Figure 7:
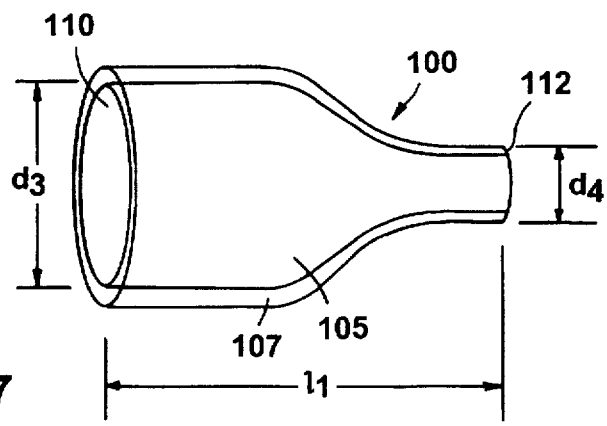
FIG. 7 is a close-up view schematic illustration of a concentrator used in the present invention.

Light beam 88 is focused into concentrator 100, a preferred embodiment of which is shown in FIG. 7. Concentrator 100 collects light from an extended area 110 and directs it to a smaller region. Concentrator 100 may include a transparent, solid, funnel-shaped piece 105 of glass, silica, or plastic, coated with a higher refractive index layer 107. Concentrator 100 functions by total internal reflection. Light rays which enter concentrator 100 through front face 110 within a critical angle are trapped and will bounce along the internal sides of layer 107 until they exit back face 112. The critical angle will be about twenty-two degrees is concentrator 100 is silica, and twenty-eight degrees is concentrator 100 is glass. Concentrator 100 may also be a hollow cone having a reflective metal interior.

Figure 1:
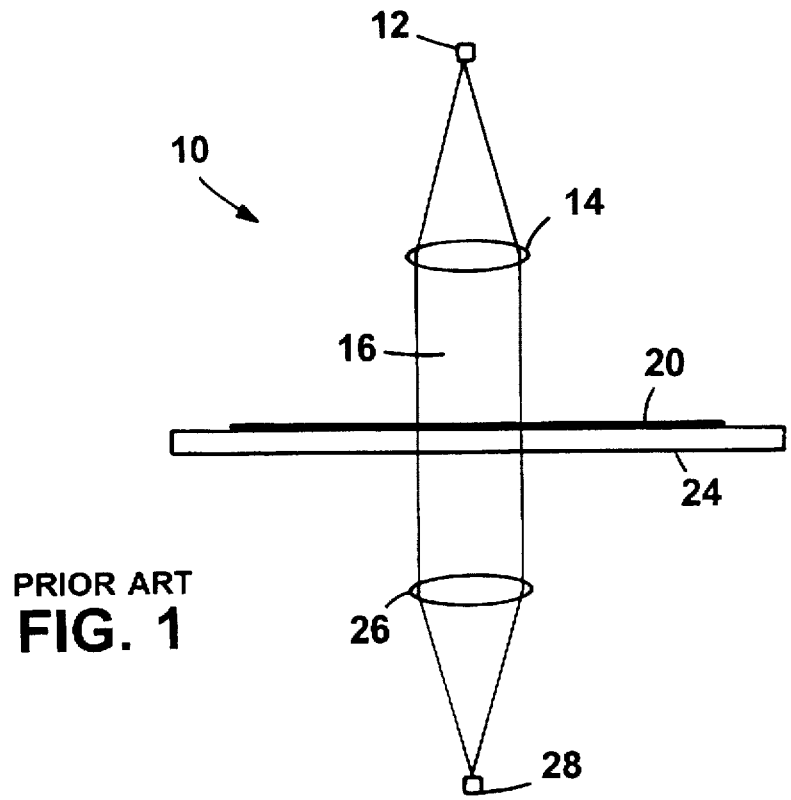
FIG. 1 is a schematic illustration of the prior art optics of a transmission analyzer.
Figure 2A:
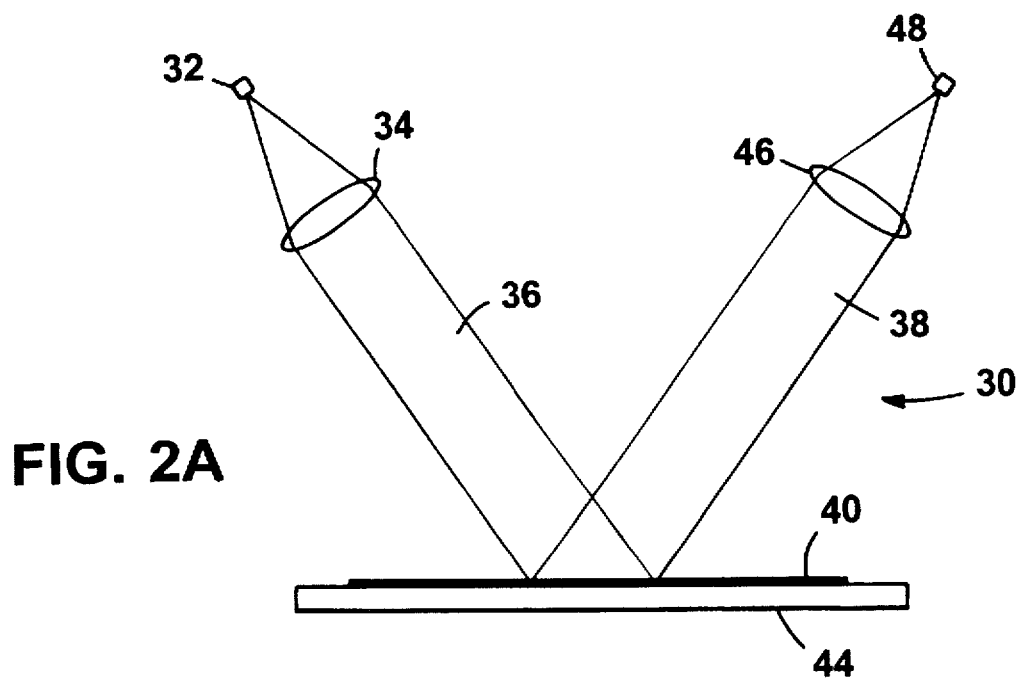
FIGS. 2A–2C are schematic illustrations of the optics of a reflection analyzer showing how a wobbling substrate affects the system.
Figure 2B:
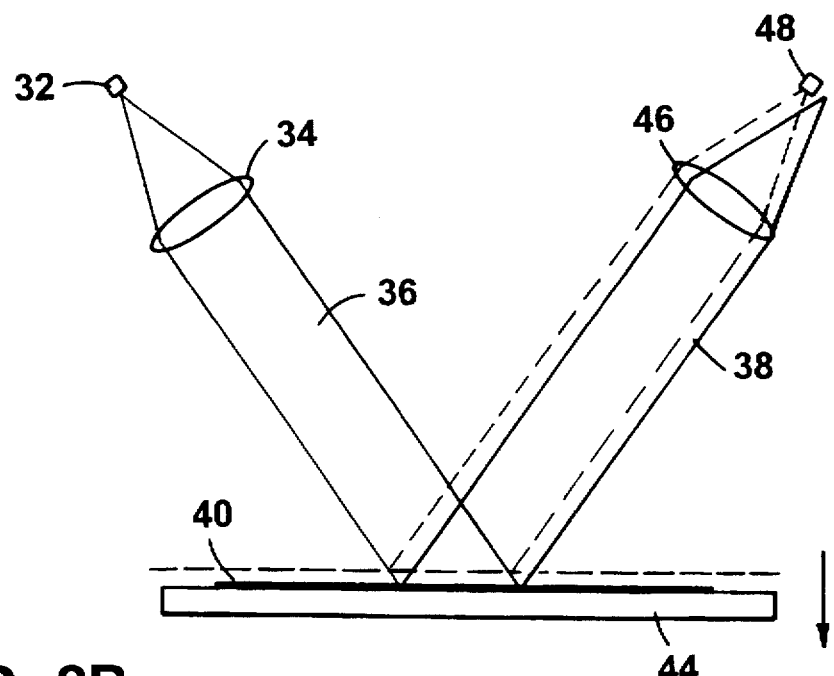
Figure 2C:
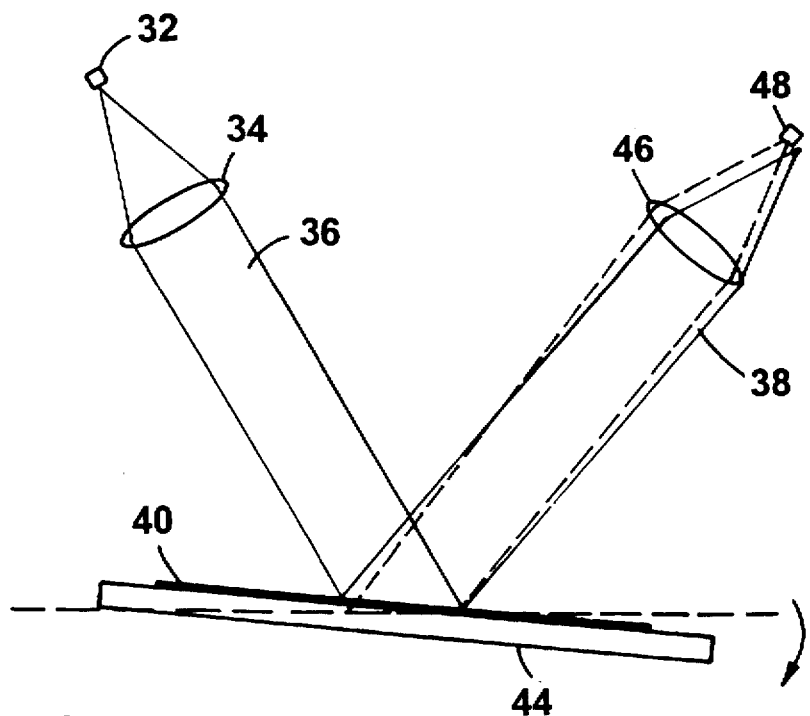

Concentrator 100 is commercially available with a "size", meaning the area ratio between the front face 110 and the back face 112, of 4:1. In order to achieve further increase in the collection area, multiple concentrators could be stacked in series. However, the preferred embodiment uses a single concentrator, about thirty millimeters long, as shown by dimension $l_1$, with a front face diameter $d_3$ of twelve millimeters and a back face diameter $d_4$ of three millimeters. If substrate 70 tilts or drops (as shown in described by FIGS. 2B and 2C), then the beam 88 will still be focused into the collection area 110, and directed to detector 98b. Thus, there is no appreciable loss of signal due to the motion of substrate 70 over rollers 75, and an accurate measurement of the reflectivity of optical coating 90 may be performed.

As shown by FIG. 5, light from the back face 112 of concentrator 100 enters an optical fiber 98a which carries the light to a detector 98b, such as a silicon photodiode or photodiode array. Back face 112 may be optically coupled to fiber 98a by coupling oil or optical epoxy, or there may be a gap. If light source 82 is full spectrum, then detector 98b may perform a full spectrograph of reflected beam 88 to determine the properties of optical coating 90. Because optical fibers 82a and 98a may be fairly long, the light source 82b and detector 92b may be placed far from the in-line system 50. This allows physically larger and more complicated detectors to be utilized.

Figure 8:
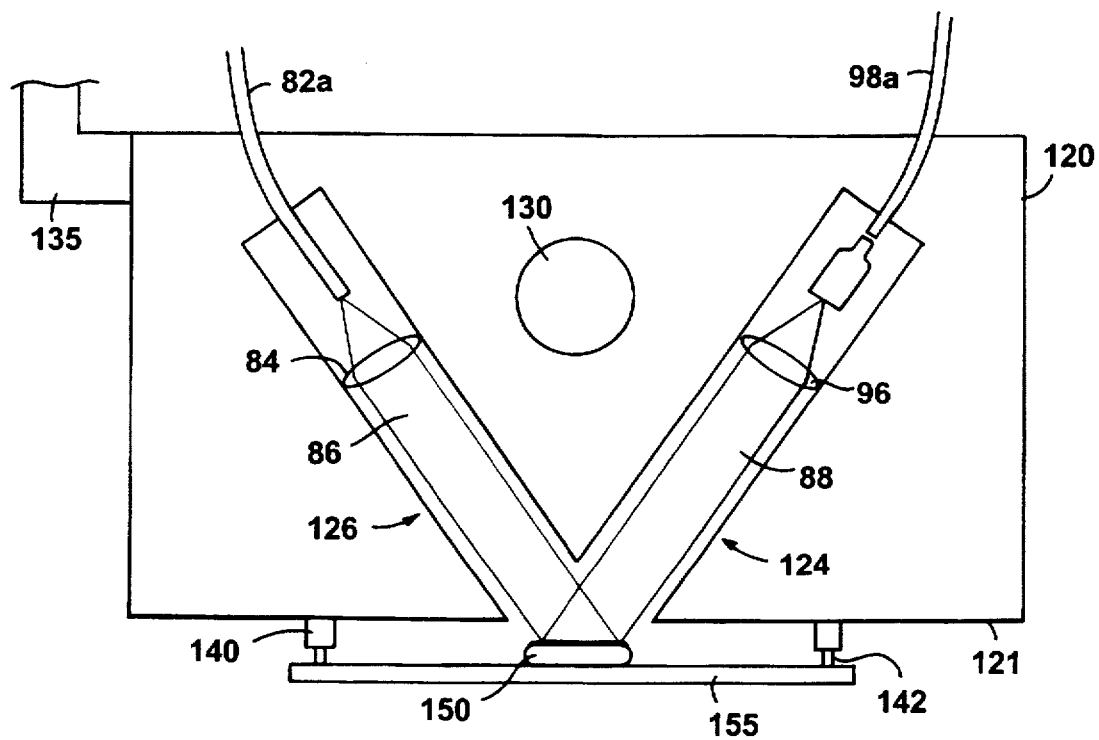
FIG. 8 is a schematic illustration of a housing for the optical analyzer of the present invention.

Due to the danger of thin film materials collecting on the optical parts and ruining the optical analyzer 80, the optical system may be contained inside a housing 120 as shown in FIG. 8. Housing 120 acts as a baffle against thin film material. Housing 120 can be a solid block of aluminum, with bores or channels 124 and 126 to mount the optical components and to carry light beams 86 and 88. Thin film material is less likely to travel up such channels and accumulate on lenses 84 and 96. In addition, because the chambers in deposition system 50 can reach very high temperatures, a line 130 may carry coolant to keep the optical components at an even temperature.

To ensure the proper distance between lenses 84, 96 and substrate 70, housing 120 could be mounted on an vertically movable arm 135 connected to ceiling 57. The distance between the front face 121 of housing 120 and the chamber floor 54 may be adjusted depending on the thickness of substrate 70, and will be as close as possible to substrate 70 without actually touching it.

This system might also be adapted to measure the reflectivity of optical coatings on individual articles 150 resting on a platform 155. Housing 120 would be lowered by arm 135 until sensors 142 on feet 140 on the bottom of housing 120 detect the surface of platform 155. The forward face 121 will be as close as possible to substrate 70 without actually touching it.

The present invention has been described in terms of a preferred embodiment. The invention, however, is not limited to the embodiment depicted and described. Rather, the scope of the invention is defined by the appended claims.

What is claimed is:

1. An optical analyzer comprising:

a light source for providing a light beam;

means for directing said light beam to a moving article having an optical coating, wherein light reflects from the article to produce a reflected light beam; and a concentrator positioned to intercept said reflected light beam, said concentrator being sized to intercept light that reflects from the article along different reflectance paths as a result of movement of the article and that passes through a collection area said concentrator being further constructed to direct the intercepted light to a detection area that has a fixed position with respect to the collection area to enable detection of light that reflects from the article along different reflectance paths as a result of movement of the article; and a detector constructed and arranged to detect light directed to said detection area.

2. The analyzer of claim 1 further including a first lens to direct light from an illuminator to said article and a second lens to focus said reflected light beam into said concentrator.

3. The analyzer of claim 2 wherein said second lens has a diameter greater than said first lens.

4. The analyzer of claim 1 wherein said concentrator comprises a transparent funnel-shaped solid section, and a coating covering an exterior surface of said funnel-shaped solid section, said coating having a higher index of refraction than said funnel-shaped solid section.

5. The analyzer of claim 1 further comprising a baffle to block the accumulation of a thin film on said concentrator.

6. The analyzer of claim 5 further including a first lens positioned inside said baffle to direct said light beam onto said article and a second lens inside said baffle to focus said reflected light beam into said concentrator.

7. The analyzer of claim 5 wherein said baffle includes a channel constructed to carry a coolant.

8. The analyzer of claim 1 wherein the fixed position of the detection area corresponds to the location of an end of an optical fiber that is coupled to said concentrator, said optical fiber having another end coupled said detector.

9. The analyzer of claim 1 wherein said provided light beam is collimated.

10. The analyzer of claim 1 wherein the collection area is larger than the detection area.

11. The analyzer of claim 10 wherein the collection area is about four times larger than the detection area.

12. An optical analyzer for measuring reflectivity of a moving article having an optical coating thereon, comprising:

a light source for providing a light beam, said light source including an illuminator and an optical fiber having an end coupled to said illuminator;

a first lens located in the path of said light beam for directing said light beam onto said article at a predetermined angle of incidence, wherein light reflects from the article to produce a reflected light beam;

a concentrator positioned to intercept said reflected light beam, said concentrator being sized to intercept light that reflects from the article along different reflectance paths as a result of movement of the article and that passes through a collection area, said concentrator being further constructed to direct the intercepted light to a detection area that has a fixed position with respect to the collection area to enable detection of light that reflects from the article along different reflectance paths as a result of movement of the article;

a second lens located in the path of said reflected light beam for focusing said reflected light beam into said concentrator;

a detector constructed and arranged to detect light directed to said detection area; and a second optical fiber having an end that is located at said detection area and is coupled to said concentrator, said second optical fiber having another end that is coupled to said detector to direct said reflected light beam to said detector.

13. An in-line sputtering system, comprising:

an evacuable chamber having two end walls, each of said end walls having an opening therein to allow passage of an article having an optical coating thereon;

a light source which provides a light beam;

means in said chamber for transporting said article between said openings and through said light beam, wherein light reflects from said article to produce a reflected light beam; and a concentrator positioned to intercept said reflected light beam, said concentrator sized to intercept light that reflects from the article along different reflectance paths as a result of movement of the article and that passes through a collection area, said concentrator being further constructed to direct the intercepted light to a detection area that has a fixed position with respect to the collection area to thereby enable detection of light that reflects from the article along different reflectance paths as a result of movement of the article.

* * * * *